United States Patent
Levison et al.

(10) Patent No.: US 6,911,305 B2
(45) Date of Patent: *Jun. 28, 2005

(54) METHOD FOR CHEMILUMINESCENT DETECTION

(75) Inventors: Derek W. K. Levison, Jackson, NJ (US); Uwe Moller, Berlin (DE); Stuart Levison, Jackson, NJ (US)

(73) Assignee: emp Biotech GmbH, Berlin (DE)

( * ) Notice: Subject to any disclaimer, the term of this patent is extended or adjusted under 35 U.S.C. 154(b) by 9 days.

This patent is subject to a terminal disclaimer.

(21) Appl. No.: 10/813,284

(22) Filed: Mar. 30, 2004

(65) Prior Publication Data

US 2005/0074815 A1 Apr. 7, 2005

Related U.S. Application Data

(63) Continuation of application No. 10/195,978, filed on Jul. 16, 2002, now Pat. No. 6,764,819.

(51) Int. Cl.$^7$ .................... C12Q 1/00; C12Q 1/42; C12Q 1/28; G01N 33/53
(52) U.S. Cl. .................. 435/4; 435/21; 435/28; 435/968; 435/975
(58) Field of Search ................. 435/4, 21, 28, 435/968, 975

(56) References Cited

U.S. PATENT DOCUMENTS

| | | | |
|---|---|---|---|
| 4,315,998 A | 2/1982 | Neckers et al. | 525/332 |
| 4,891,324 A | 1/1990 | Pease et al. | 436/519 |
| 5,386,017 A | 1/1995 | Schaap | 536/18 |
| 5,516,636 A | 5/1996 | McCapra | 435/6 |
| 6,143,514 A | 11/2000 | Ullman et al. | 435/28 |
| 6,613,578 B1 | 9/2003 | Moller et al. | 422/52 |
| 6,764,819 B2 * | 7/2004 | Levison et al. | 435/4 |

OTHER PUBLICATIONS

Schubert et al.; Non–radioactive detection of oligonucleotides probes by photochemical amplification of dioxetanes; Nucleic Acids Research, 1995, vol. 23, No. 22, 4657–4663.

* cited by examiner

*Primary Examiner*—Louise N. Leary
(74) *Attorney, Agent, or Firm*—Hoffmann & Baron, LLP

(57) ABSTRACT

The invention provides chemiluminescent assays that incorporate a film including at least one chemiluminescent precursor immobilized therewith which produces a triggerable chemiluminescent compound, the film being free of compounds which generate singlet oxygen and being adapted for use with a sensitizer-labeled agent or agent probative of the analyte.

56 Claims, 9 Drawing Sheets

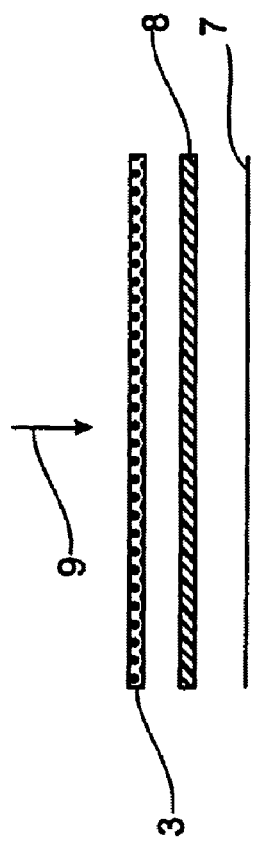
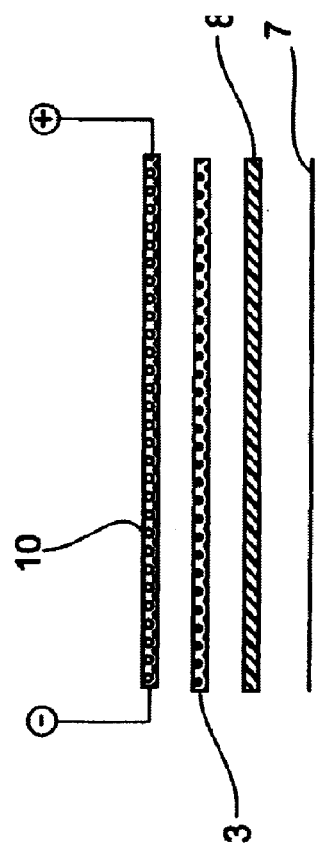

METHOD FOR CHEMILUMINESCENT DETECTION

CROSS REFERENCE TO RELATED APPLICATIONS

This application is a continuation of U.S. application Ser. No. 10/195,978, filed Jul. 16, 2002, now U.S. Pat. No. 6,764,819, the contents of which are incorporated herein by reference.

FIELD OF THE INVENTION

The present invention relates to chemiluminescent assays that incorporate a which includes a chemiluminescent precursor component immobilized therewith which produces a triggerable chemiluminescent compound for detection of a target molecule.

BACKGROUND OF RELATED TECHNOLOGY

Recently a variety of non-isotopic labeling methods have been developed to replace radioactive labels in DNA probe-based assays. It is most common in such methods to use marker enzymes to detect nucleic acid probes using either colormetric, chemiluminescent, bioluminescent or fluorescent methods. Each of these methods have been used reliably for both hybridization of DNA probe-based assays for nucleic acid detection as well as in solid-phase immunochemical a s says wherein the target molecule is typically an antigen of interest.

Regardless of the type of non-isotopic detection method used, the labels are typically measured directly with fluorophores (without use of enzymes) or indirectly using enzyme amplification schemes. A clear advantage of an indirect labeling scheme is the increased sensitivity one achieves through enzymatic amplification of the signal. However, a disadvantage of such methods as they are currently practiced in the field is that many steps are required in the assay protocol, requiring more time to complete the assay. Moreover, a greater number of reagents are required which means greater cost. In addition, where the method of detection is enzyme-based, the enzyme's activity, stability and its shelf life need to be considered if one is to expect optimum performance of the assay.

Chemiluminescence detection relies on a chemical reaction that generates light. It is this method which is now widely used for both nucleic acid detection as well as solid-based immunodetection due to its high sensitivity and wide variety of analysis methods ranging from manual film reading to instrumentation for processing images. Most commercially available chemiluminescent detection systems employ enzyme conjugates to increase detection sensitivity through amplification of the signal and, therefore, suffer from the same disadvantages described above.

In view of the simplicity of chemical reactions relative to enzymatic reactions, it would be desirable to achieve chemiluminescent signal amplification by chemical as opposed to enzymatic means. Moreover, non enzymatic systems have the advantage over enzyme-mediated systems of faster kinetics which result in peak light output within seconds. U.S. Pat. No. 5,516,636 to McCapra and a later publication by Schubert (Nucleic Acids Research, 1995, Vol. 23, No. 22 p. 4657) describe the use of sensitizer-labeled oligonucleotide probes for the detection of nucleic acid target molecules. In a solid phase DNA probe assay, a DNA target molecule is bound to a membrane and hybridized to a sensitizer-labeled oligonucleotide complementary in sequence to the target DNA. The membrane is subsequently contacted with an olefin. Upon exposure of the membrane to ambient oxygen and light, the sensitizer molecules become excited and transfer their excess energy to ambient oxygen for formation of singlet oxygen. The singlet oxygen therein produced reacts with the olefin on the membrane to form a stable 1,2-dioxetane in the area of the hybridization zone which when subsequently exposed to heat, chemical treatment or enzymatic treatment decomposes to emit light. Thus, oligonucleotides labeled with sensitizer are able to amplify the dioxetane concentration based on repeated excitation/oxygen quenching cycles to achieve a high level of sensitivity.

Prior art chemiluminescent assays employing sensitizers have generally required that a sensitizer-labeled probe hybridized to an analyte on a membrane be brought in contact with olefin for reaction to form a decomposable dioxetane. The membrane containing the analyte is then triggered by an activating source (e.g. base and/or heat) to produce a signal. The disadvantage of this format is that, because the analyte must be subjected to heat and/or base, it is not further utilized for additional testing and analysis.

U.S. Pat. No. 6,143,514 discloses a matrix having incorporated therein a label capable of being modified by a singlet oxygen and a non-photoactivatable catalyst (e.g. an enzyme) that is capable of catalyzing the formation of singlet oxygen from hydrogen peroxide. The catalyst coated matrix is incubated with assay medium suspected of containing hydrogen peroxide to permit the hydrogen peroxide to react with the catalyst to form singlet oxygen. The reaction of singlet oxygen with the label is determined, the reaction thereof indicating the presence of a compound capable of generating hydrogen peroxide. One disadvantage of this assay is that, because it is enzyme-based, the activity of the enzyme, its stability and its shelf-life need to be monitored as discussed above.

It would be advantageous to provide a method of performing a sensitizer-mediated solid phase chemiluminescent assay which would allow for reuse of a membrane-bound analyte. This is particularly desirable when amounts of available analyte for testing are limited. Such a method would preferably employ a membrane containing a solid olefin immobilized on or impregnated with, the membrane being suitable for use in both solid phase nucleic acid assays and immunoassays and, further, being able to be analyzed by methods ranging from manual film reading to instrumentation for processing images.

SUMMARY OF THE INVENTION

In one aspect of the invention, there is provided a film component for chemiluminescent assays including a solid film substrate and at least one chemiluminescent precursor immobilized therewith which produces a triggerable chemiluminescent compound, the film component being free of compounds which generate singlet oxygen and being adapted for use with a sensitizer-labeled analyte or a sensitizer-labeled agent probative of the analyte.

The invention further provides a method of detecting target nucleic acid molecules using chemiluminescence. The method includes providing a first film having a complex that includes a polynucleotide analyte to which is bound, either directly or indirectly, a sensitizer. For example, the sensitizer can be bound directly to the polynucleotide analyte or a sensitizer-labeled probe can be bound to the polynucleotide analyte. The sensitizer-labeled probe is probative of the analyte, and can be complementary in sequence to the polynucleotide analyte. The method further includes providing a second film including at least one solid chemiluminescent precursor component immobilized therewith that is capable of producing a triggerable chemiluminescent compound. Also included in the method is the step of placing the provided first and second films in sufficient proximity to each other to permit singlet oxygen produced from excitation of the sensitizer on the first film and to react with the chemiluminescent precursor on the second film. The method further involves: exposing the films to suitable conditions (e.g., light and oxygen) to form the triggerable chemiluminescent compound on the second film; allowing the triggerable chemiluminescent compound to be triggered by an activating source to produce a detectable light signal on the second film; and detecting and/or recording the resultant signal on the second film.

Furthermore, another aspect of the present invention relates to a method of preparing a chemiluminescent assay that includes the steps of: providing a first film having a complex that includes polynucleotide analyte bound to a sensitizer or a sensitizer-labeled probe; and providing a second film including at least one solid chemiluminescent precursor component immobilized therewith that is capable of producing a triggerable chemiluminescent compound. The method further includes: positioning the first and second films in overlapping contact with each other, exposing the contacted films to suitable conditions (e.g., light and oxygen) to form the triggerable chemiluminescent compound on the second film; and allowing the triggerable chemiluminescent compound to be triggered by an activating source to produce a detectable light signal on the second film.

Also provided is a chemiluminescent assay kit that includes a film component including a solid film substrate and at least one chemiluminescent precursor immobilized therewith that is capable of producing a triggerable chemiluminescent compound, the film component being free of compounds which generate singlet oxygen and being adapted for use with a sensitizer-labeled polynucleotide analyte or a sensitizer-labeled agent probative of the analyte. The kit further includes a sensitizer-labeled nucleotide or a sensitizer-labeled primer, which can be either a random or a specific primer.

BRIEF DESCRIPTION OF THE DRAWINGS

FIG. 6B shows a perspective of a sandwich assay format wherein the inventive second film containing the triggerable chemiluminescent compound formed in FIG. 6A is exposed to a triggering source for capture of a light signal on photographic film.

FIG. 7 is a perspective view of a sandwich assay format that includes a first having bound thereto a target molecule labeled directly or indirectly with a sensitizer, a second film in accordance with the present invention that includes a solid chemiluminescent precursor component capable of forming a triggerable chemiluminescent compound, and a third film for contact with the film of the present invention, the third film including at least one solid chemical component which when acted upon by an energy source releases an activating substance to trigger the chemiluminescent compound.

DETAILED DESCRIPTION OF THE INVENTION

Figure 1:
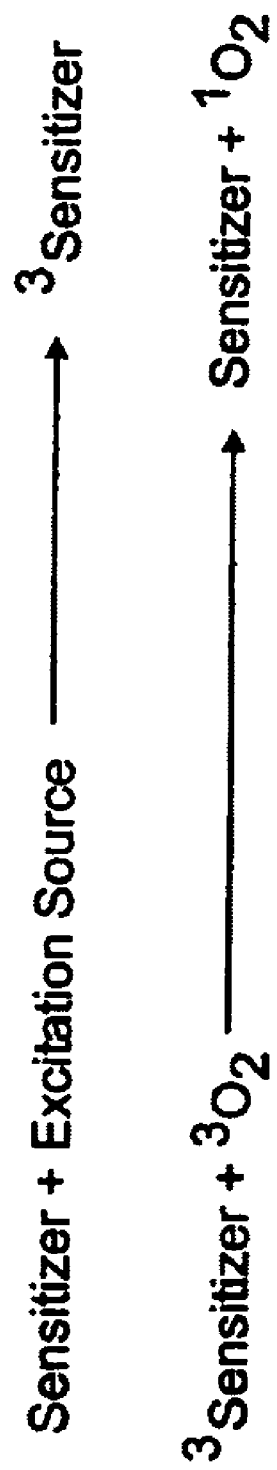
FIG. 1 shows the reactions involved in the sensitizer-catalyzed generation of singlet oxygen.

As defined here in, the term "analyte" refers to the compound or composition to be detected. The analyte may be a polynucleotide, peptide, polypeptide, protein, antibody, antigen, ligand, receptor, hapten, saccharide, or polysaccharide. Furthermore, the analyte can be a part of a cell, such as a bacteria or a cell bearing a blood group antigen or an HLA antigen or a microorganism.

The term "polynucleotide analyte" as used herein refers to a polymer comprising multiple nucleotides and includes, but is not limited to: oligonucleotides, polynucleotides, DNA, RNA, DNA-RNA duplexes and analogs of any one of these. For example, the analyte can be a DNA analog, such as a peptide nucleic acid (PNA).

Sensitizer label, photosensitizer label, and the like as defined herein is a substance which when exposed to suitable conditions causes light to be produced. In one embodiment when appropriately combined with molecular oxygen, light of an appropriate wavelength, and a chemiluminescent precursor, the sensitizer label causes light to be produced. In one sense, a sensitizer can be a molecule with a chromophore that is capable of absorbing light so that it becomes electronically excited. In another embodiment, a sensitizer label, when exposed to electrical or electromagnetic stimulation, causes light to be produced.

The term chemiluminescence, chemiluminescent and the like refers to the production of light by way of a chemical reaction. It may further be defined as the light emitted during the time that electronically excited products of chemical reactions return to the ground state.

In one aspect of the invention, there is included a film for use in the detection of target molecules via chemiluminescent solid phase and gel-type assays. The film component includes a solid film substrate and at least one chemiluminescent precursor immobilized therewith which produces a triggerable chemiluminescent compound, the film component being free of compounds which generate singlet oxygen and being adapted for use with a sensitizer-labeled analyte or sensitizer-labeled agent that is probative of the analyte.

The chemiluminescent precursor may be immobilized to the film by direct, indirect, covalent or non-covalent binding. The surface of the film substrate may be polyfunctional. Furthermore, functional groups may be incorporated into the film for binding to available or incorporated functional groups on the chemiluminescent precursor. Functional groups may include, but are not limited to, the following groups: carboxyl, hydroxyl, cyano, amino, ethylene, mercapto, epoxide, and aldehyde groups. In one aspect the chemiluminescent precursor may be immobilized with the film substrate by means including, but not limited to, dipping, soaking, painting, pipetting, spotting or spraying the precursor on the substrate, followed by drying.

The target molecule may be a nucleic acid, such as RNA or DNA. In addition, the film and its method of use may be used in solid-phase immunoassays in which the target molecule can be either antibody or antigens and wherein a corresponding sensitizer-labeled probe may be antigen or antibody, respectively. In the context of this invention, use of the term "film" includes membranes, filter paper and gels. Films may be of any useful thickness or porosity depending on their specific application. Such films are inclusive of, but not limited to, textile films, glass films, metal films, paper films, cellulose films, polyacrylamide and agarose gels. In particular, it is envisioned that nylon, nitrocellulose, or PVDF membranes or filter paper may be useful for practice of the present invention.

The inventive aspects of the present invention are achieved, in part, by the provision of an analyte or agent probative of the analyte bearing a sensitizer label. In preferred embodiments of the inventive methods, a sensitizer provided with molecular oxygen and light of an appropriate wavelength, may produce singlet oxygen in accordance with the reactions shown in FIG. 1. The sensitizer achieves the triplet state when excited by one or more of the stimulus selected from the following: radiation, electron transfer, electrolysis, and electroluminescence. In desired embodiments, the radiation includes light having a wavelength from about 30 nm to about 1,100 nm.

With further reference to FIG. 1, the excited sensitizer interacts with an acceptor molecule. In one desired embodiment, the acceptor molecule is molecular oxygen in the ground state. The photosensitizer in its triplet state (excited state) is capable of converting ground-state oxygen (a triplet) to an excited singlet state, the singlet oxygen capable of resulting in the production of the detectable signal which can be monitored. In the assays of the present invention, the amount of signal produced may be measured, wherein the amount to the signal is correlated to the amount of analyte present in a given sample.

Figure 2:
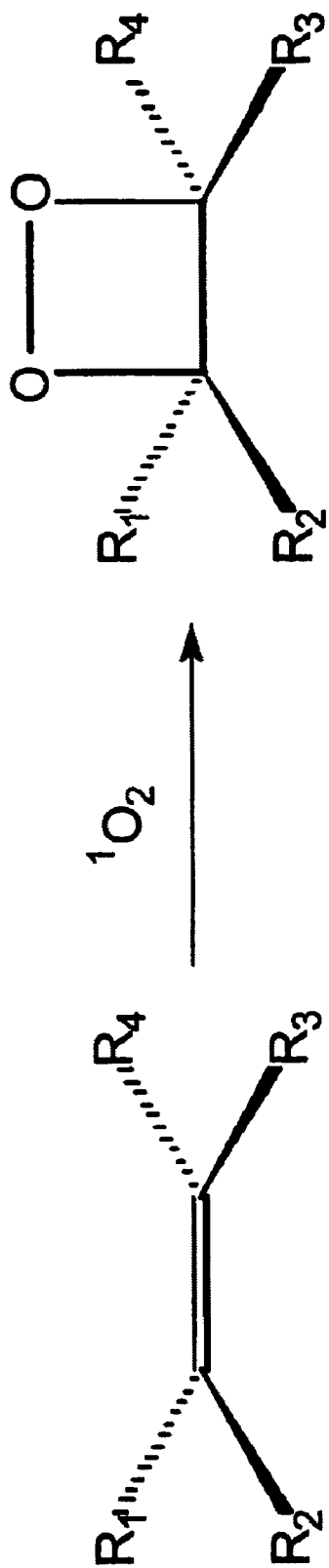
FIG. 2 shows the reaction of singlet oxygen with a chemiluminescent olefin to form a 1,2-dioxetane.

In preferred embodiments of the present invention, the singlet oxygen produced as shown in FIG. 1 reacts with an olefin to form a dioxetane. The olefin is the chemiluminescent precursor immobilized with the film of the present invention which produces a triggerable chemiluminescent compound. In one embodiment, the singlet oxygen may react by a 1,2-cycloaddition with an olefin to give a 1,2-dioxetane (the triggerable chemiluminescent compound), as shown in FIG. 2. The dioxetane formed is a metastable reaction product, which is capable of decomposition with the simultaneous or subsequent emission of light, usually within the wavelength range of 250–1,200 nm.

Figure 3:
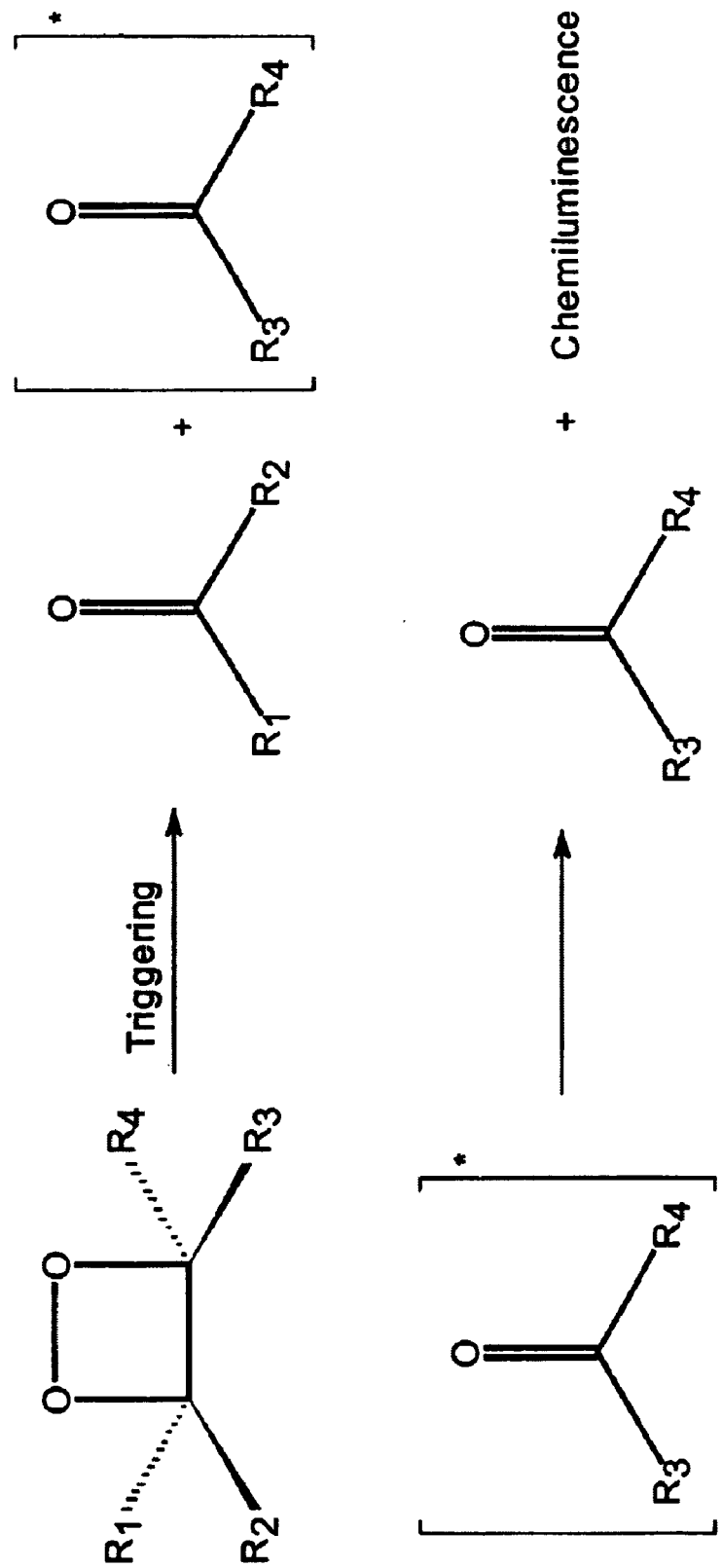
FIG. 3 shows the induced decomposition of the 1,2-dioxetane formed in FIG. 2 by an appropriate trigger to release light. Preferred triggering conditions include a change in pH or temperature.

It is noted that for the olefin and metastable dioxetane shown in FIGS. 2 and 3, definitions of suitable R substituents can be found in, but are not limited to, those in U.S. Pat. No. 5,386,017. For example, $R_1$ maybe selected from alkyl, alkoxy, aryloxy, dialkyl or aryl amino, trialkyl or aryl silyloxy groups and $R_2$ is an aryl group substituted with an X oxy-group, wherein the 1,2 dioxetane forms an unstable oxide intermediate 1,2-dioxetane compound when triggered to remove X by an activating agent so that the unstable 1,2,dioxetane compound decomposes to form light and two carbonyl-containing compounds (shown in FIG. 3) wherein X is a labile group which is removed by the activating agent to form the unstable oxide intermediate and wherein $R_3$ and $R_4$ are selected from aryl and alkyl groups which can be joined together as spirofused polycyclic alkyl and polycyclic aryl groups.

Referring now to FIG. 3, some dioxetanes decompose by heating, chemical, electrical, electrochemical, electrostatic, or enzymatic means to produce light. For example, the 1,2-dioxetane shown in FIG. 3 may be cleaved thermally to carbonyl-containing products. In a further embodiment, the triggerable chemiluminescent compound may be triggered by exposure to a chemical base.

Figure 4:
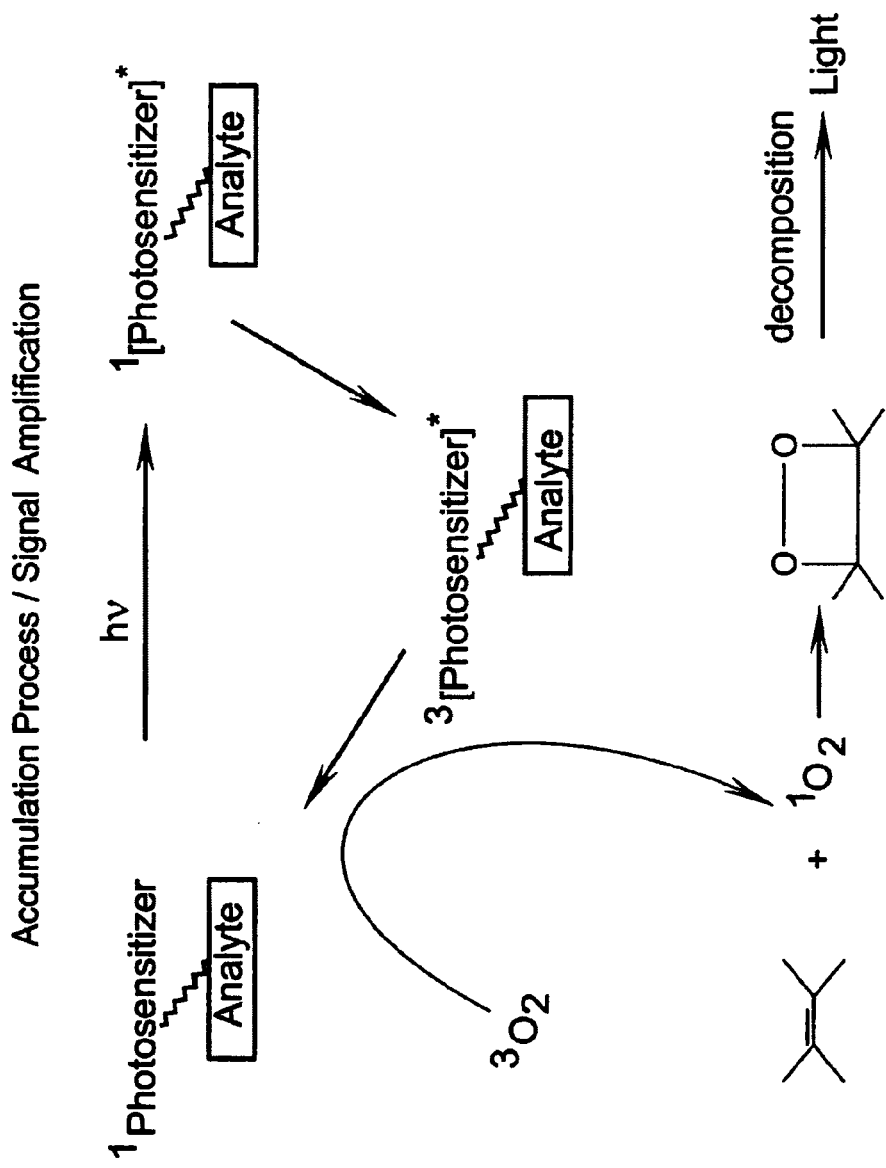
FIG. 4 shows chemiluminescent signal amplifications by a sensitizer means, the sensitizer being conjugated to the analyte (substance to be detected) or, alternatively, conjugated to a probe that specifically binds to the analyte.

The present invention has the advantage of amplifying the amount of chemiluminescent compound (dioxetane) produced in the assay; this results in signal enhancement. This is illustrated in FIG. 4. Since the acceptor molecule of the energy (e.g., molecular oxygen) is present in great excess over the sensitizer label, the continuous recycling of the photosensitizer during irradiation by the exciting light will lead to amplifications several-fold over the concentration of the label. The signal is created as a result of the donor-acceptor interaction between the excited triplet state sensitizer and the acceptor molecule (ground-state molecular oxygen). The sensitizer is allowed to return to its original state after it has passed its energy to the acceptor. Preferably, this occurs by a triplet-triplet annihilation via CIEEL mechanism (chemically induced electron exchange luminescence). Because the sensitizer is still present in association with ground-state oxygen, it is available for another excitation, followed by energy transfer to the acceptor for the production of an even greater signal. This type of excitation and energy transfer may be repeated many times within a very short period of time so that the use of a sensitizer as a label on the analyte or agent probative of the analyte provides the added advantage of amplifying the signal, and thus increasing the sensitivity of the assay.

Figure 5:
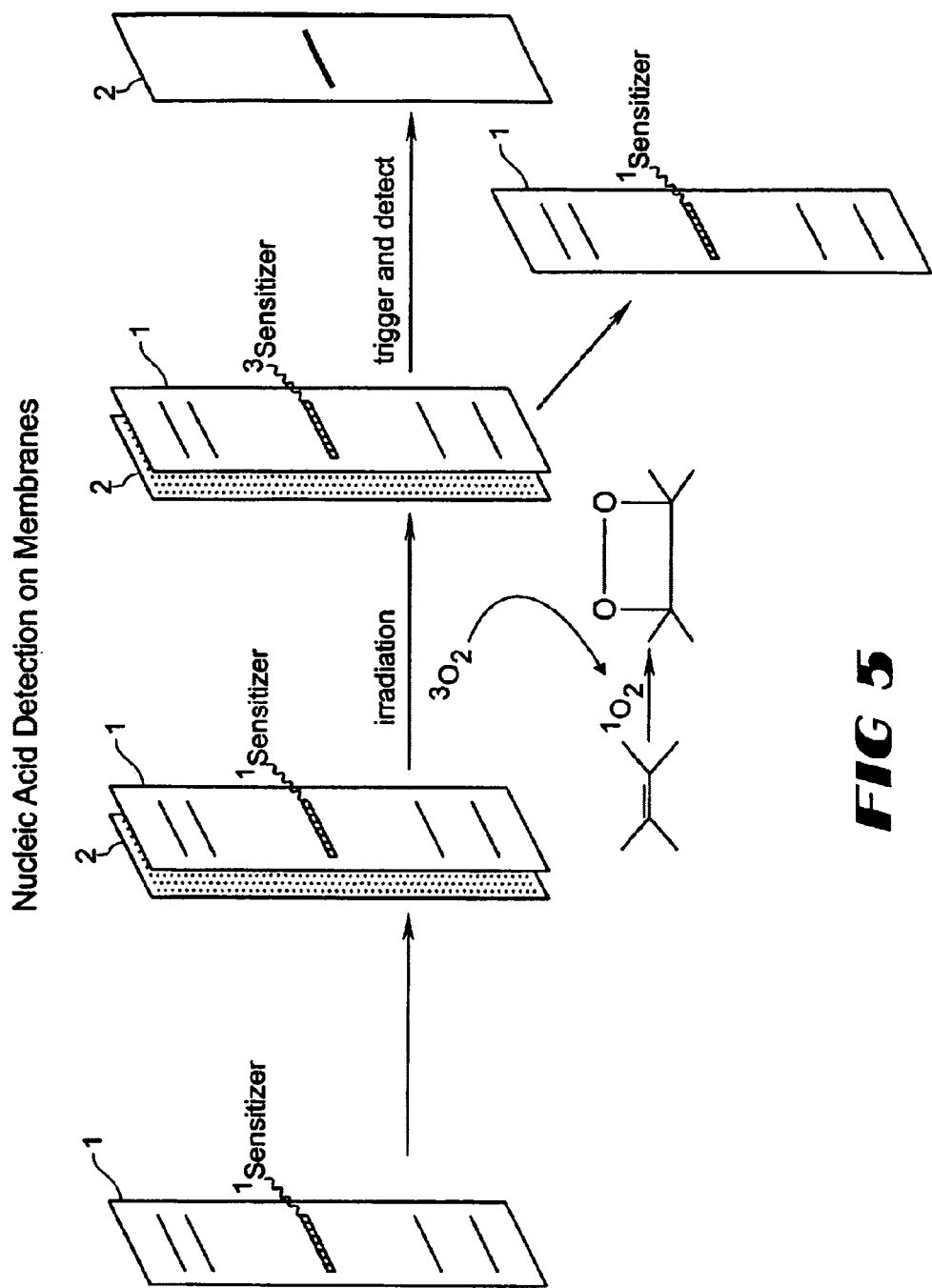
FIG. 5 shows solid phase chemiluminescent detection of labeled target DNA employing a film 2 according to the present invention that includes a solid chemiluminescent precursor component, such as a chemiluminescent olefin that is capable of forming a triggerable chemiluminescent compound.

We refer now to FIG. 5, which shows one embodiment of a chemiluminescent method according to the present invention for detecting target molecules that employs a film of the present invention. The assay shown is for nucleic acid detection on membranes. In one embodiment, sensitizer-labeled analyte may be immobilized directly on a first film for detection. Alternatively, immobilized target DNA may be bound to an agent probative of the analyte, the probative agent bearing the sensitizer label. For example, in one embodiment the sensitizer-labeled agent probative of the analyte is a probe complimentary in sequence to the analyte. In particular, the probative agent may have an area on the surface or in a cavity which specifically binds to and is, thereby, defined as complimentary with a particular spatial and polar organization of the other molecule (i.e., analyte). Exemplary of this type of specific binding are antibody-antigen interactions, enzyme-substrate interactions, polynucleotide interactions, and so forth. As shown in FIG. 5, first film 1 that includes the bound target is brought into contact with film 2 of the present invention that includes the immobilized chemiluminescent olefin. In particular, film 1 and inventive film 2 should be placed in sufficient proximity to each other to permit singlet oxygen produced from excitation of the sensitizer on the first film to react with the chemiluminescent precursor (e.g. olefin) on the inventive film. Following exposure of the films to light (of an appropriate wavelength) and oxygen, a triggerable chemiluminescent compound is formed on the inventive second film. The irradiation must be of a wavelength appropriate to excite the particular sensitizer used as the label, such as 670 nm for methylene blue. The sensitizer becomes electronically excited to its triplet state and transfers its excess energy to ground-state oxygen ($^3O_2$) for the production of a singlet oxygen. The singlet oxygen therein produced reacts with the chemiluminescent precursor (e.g. olefin) on film 2 of the present invention to form a triggerable chemiluminescent compound (for example, a metastable 1,2-dioxetane) on film 2 of the invention in the area corresponding to the analyte zone, which when subsequently exposed to heat, chemical treatment or enzymatic treatment, decomposes to emit light as a signal on the film 2. It is important to note that only film 2 of the present invention undergoes the triggering process. Film 1, containing immobilized analyte, is not exposed to the triggering conditions. As such, Film 1 containing immobilized analyte may be used for further analysis. In one embodiment, a triggerable 1,2-dioxetane on film 2 may be exposed to chemical treatment with a base at a pH of about 11.0. Alternatively, a triggerable 1,2-dioxetane may be activated by heating to a temperature from about 50° C. to about 100° C. The signal may be detected in the form of a band on x-ray film. In a further embodiment, the light energy produced may be detected by means of a photoelectric cell. Although the signal may be detected optically, it is preferred that the signal is recorded by means of a light-sensitive film, photoelectric cell, or other suitable means.

Figure 6A:
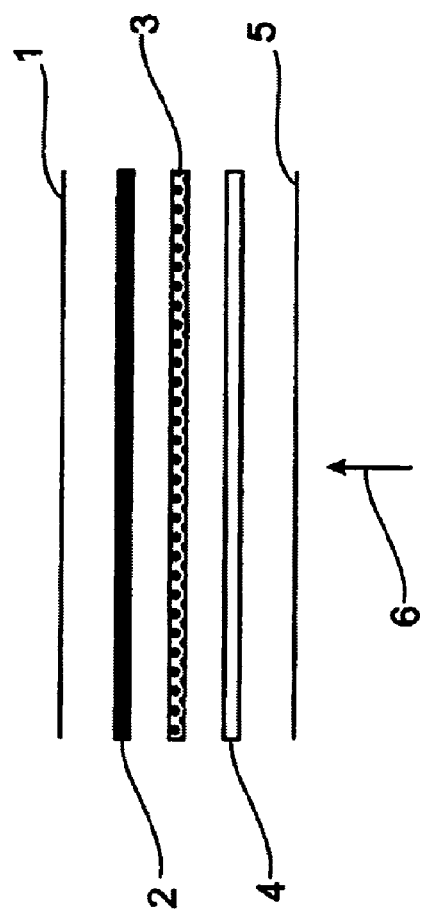
FIG. 6A shows a perspective of a sandwich assay format that includes a first film having bound thereto a target molecule that is directly or indirectly labeled with a sensitizer and a second film corresponding to the film of the present invention, wherein a triggerable chemiluminescent compound is formed on the second film in response to an energy source as per the reaction shown in FIG. 2.

Referring now to FIG. 6A, there is a depiction of a sandwich formation useful for the proper positioning of the film containing the immobilized target molecule and the inventive film. In this figure, film 4 represents a film having a target molecule thereon that has been labeled directly or indirectly with a sensitizer. Film 3 represents the second film of the present invention which contains the chemiluminescent precursor (olefin) for forming a triggerable chemiluminescent compound. Films 4 and 3 are positioned in overlapping relationship and in intimate contact therebetween. Film 2 in this figure represents a non-transparent black paper. The entire sandwich structure is supported by glass plates 1 and 5. It is noted that transparent film 5 allows irradiation to pass therethrough to cause the olefin on Film 3 to form a triggerable dioxetane. Mesh-type films would also be suitable for this purpose. Moreover, translucent films may also be useful in this regard Energy source 6 is applied to the sandwich format in order to excite the sensitizer label on film 4, which leads to the production of a triggerable chemiluminescent compound on film 3 in the target zone. As noted above, various types of energy sources are useful such as including, but not limited to, irradiation with light of a wavelength suitable to excite the particular sensitizer label associated with the analyte. The transmission of irradiated light 6 is suitable to cause the sensitizer to produce singlet oxygen. The singlet oxygen thus produced then travels from the membrane with the sensitizer through space to the inventive membrane including the chemiluminescent precursor, where it reacts with the precursor to produce a triggerable chemiluminescent compound in the analyte zone.

With reference now to FIG. 6B, there is a depiction of a sandwich formation useful for the proper positioning of film 3 from FIG. 6A which contains a triggerable chemiluminescent compound thereon, with a light-sensitive photographic film 7. A transparent protective film 8 may be positioned between film 3 and photographic film 7. The triggerable chemiluminescent compound (e.g. metastable dioxetane) present on film 3 is exposed to a triggering source 9 for capture of a light signal on photographic film 7. As noted above, various triggering sources may be appropriate, including enzymatic, heat, or chemical means. Whereas positioning of photographic film 7 in this manner allows for capture of a chemiluminescent signal, it should be noted that other means of signal detection and capture may be utilized in place of the photographic film Electronic devices may be useful in this regard.

In FIG. 6B, the membrane containing the precursor/chemiluminescent compound is separately triggered in response to an activating source 9 to produce a chemiluminescent signal. Of note is the fact that the original membrane containing the analyte does not undergo the triggering process and can be further utilized for additional testing.

It is well within the contemplation of the present invention that an activating film may be combined in sandwich formation with an inventive membrane containing the triggerable chemiluminescent compound formed in FIG. 6A and a photographic film. In this respect, it is noted that copending, commonly owned U.S. application Ser. No. 09/913,653, which is herein incorporated by reference in its entirety, teaches the combined use of heat and chemical treatment as a means of decomposing a triggerable chemiluminescent compound (e.g. a dioxetane). Because heating a caustic solution of chemical base to at or near boiling temperatures would be both dangerous and impractical, this prior application teaches the use of an activating film that may contain a solid chemical component immobilized on or impregnated therewith, which when acted upon by an energy source, such as heat, releases an activating substance capable of decomposing a triggerable chemiluminescent compound to produce a chemiluminescent signal for the detection of a target molecule.

A sandwich formation useful for the proper positioning of the inventive membrane, activating film, and photographic film is shown in FIG. 7. Film 3 represents the inventive membrane with a triggerable chemiluminescent compound formed in FIG. 6A thereon. Film 10 represents the activating film just described that releases the triggering substance. Film 7 represents a photographic film. A transparent plastic film 8 is placed between the film 3 and film 7 to protect the photographic film. FIG. 7 shows application of a voltage to activating film 10 to cause release of the triggering substance. This application of electrical energy may serve to apply heat to or cause ion flow in the solid chemical component on film 10.

Olefins having the structure shown below have been described in U.S. Pat. No. 5,386,017 to Schaap.

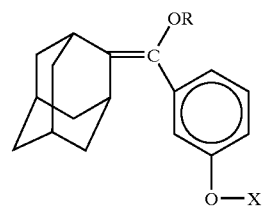

These olefins are suitable for practice of the present invention. However, this invention is not limited to these olefins. Treatment of a stable dioxetane with an appropriate activating agent produces chemiluminescence. The X group on the dioxetane represents a labile leaving group. This group may be activated or chemically cleaved by chemical means in one example. Examples of typical X groups which can be removed chemically, as well as enzymatically are shown in U.S. Pat. No. 5,795,987. Useful X-oxy protecting groups include, but are not limited to, hydroxyl, alkyl or aryl, carboxyl ester, inorganic oxy-acid salt, alkyl or aryl silyloxy and oxygen pyranocide. Additional examples of protecting groups, as well as the corresponding cleavage/activating agents useful for removal of X can also be found in the standard treatise on protecting groups (Greene and Vuts, in Protective Groups in Organic Synthesis, 1999).

In one embodiment, the dioxetane is caused to decompose by an appropriate activating source, such as chemical means. For example, the activating source may be a base and/or heat. The base may be a solid chemical component which is incorporated into the activating film described above.

For example, the choice of the solid chemical component will depend largely on the X group on the dioxetane shown in the formula above. In the case of X being hydrogen, deprotonation will be required in order to decompose the dioxetane for signal formation. In such a case, a base would be needed. The solid chemical component on the activating film, when exposed to the proper energy source, would desirably release a base. For example, the solid chemical component on the activating film may be ammonium carbonate, which when exposed to heat liberates a gaseous base ($NH_3$), water, carbon dioxide and, if $NH_3$ reacts with water, hydroxy (OH—) anions. The base components released then act to deprotonate the dioxetane resulting in signal formation.

In general, the activating film 10 in FIG. 7 may include a solid chemical component selected from acids, bases, salts, enzymes, inorganic and organic catalysts, and electron donor sources, each when acted upon by an energy source cause release of an activating substance for production of a chemiluminescent signal on the film of the present invention. The signal may be captured by photographic film as described above. The energy source used for release of the activating substance may be chosen from thermal energy, electromagnetic energy, electrical energy, mechanical energy, and combinations thereof.

As described above, the analyte is the substance to be detected. In one embodiment, this substance may be selected from the following: polynucleotide, protein, saccharide, polysaccharide, hapten, peptide, polypeptide, antigen and antibody. Polynucleotide analytes refers to polymers including multiple nucleotides and include, but are not limited to, oligonucleotides, polynucleotides, DNA (single-stranded or double-stranded), DNA-RNA duplexes, m-RNA, r-RNA, t-RNA and analogs of any of these, such as peptide nucleic acids (PNAs). The analyte under detection may also include substances which are capable of binding to these polynucleotides, such as including, but not limited to, enzymes, activators, repressors, repair enzymes, polymerases, and nucleases. The analyte may be found directly in a sample from a patient, such as a biological tissue or body fluid. The sample can either be directly used or may be pretreated to render the analyte more detectable.

A sensitizer label may be incorporated by such means as PCR amplification within the analyte or within the agent probative of the analyte (i.e., probe). In one embodiment, a polynucleotide analyte may be labeled (directly or indirectly) by incorporation of a photosensitizer-labeled nucleotide into the analyte or probe during a nucleic acid amplification reaction. In a further embodiment, a polynucleotide analyte or probe may be labeled by incorporation of a photosensitizer-labeled primer during a target amplification reaction In alternative embodiments, a primer extension reaction, or an in vitro transcription reaction may be used to incorporate a photosensitizer-labeled nucleotide or photosensitizer-labeled primer within the analyte or probe. The primers may be either random or specific primers. The aforementioned reactions are described by Ausubel, F. M. et al. (eds.) In Current Protocols in Molecular Biology, John Wiley & Sons, Inc., New York (1999). It is further anticipated that the analyte or a specific oligonucleotide probe that is probative of the analyte may be aminofunctionalized so as to be labeled by reaction with an NHS ester form of a sensitizer.

Polymerase chain reaction (PCR) is a method for in vitro amplification of a segment of DNA described by Saiki, et al. in Science 239: 487 (1988), Mullis et al. in U.S. Pat. No. 4,683,195, Ausubel, F. M. et al. (Eds.), Current Protocols in Molecular Biology, John Wiley & Sons, Inc., New York (1999), and Wu, R. (Ed.), Recombinant DNA Methodology II, Methods Enzymol., Academic Press, Inc., New York, (1995). In general, a PCR reaction contains template DNA with the target sequence to be amplified, two primers complementary in sequence to the target DNA, nucleotides, buffer, and a thermostable DNA polymerase. The reaction mixture is subjected to several cycles of incubation at temperature for denaturation, annealing and elongation, resulting in exponential amplification of the target DNA. The oligonucleotides primers may be synthesized by methods known in the art. Suitable methods include those described by Caruthers in Science 230:281–285 (1985) and DNA Structure, Part A: Synthesis and Physical Analysis of DNA, Lilley, D. M. J. and Dahlberg, J. E. (eds), Methods Enzymol., 211. Academic Press, Inc., New York (1992). The amplified fragment may be cloned, sequenced and may be further amplified to obtain a longer nucleic acid molecule.

Nucleic Acid Sequence Based Amplification (NASBA; described in EP 0329822) is a method that may be used for amplification of RNA. In particular, this method is a specific, isothermal method of nucleic acid amplification that involves the coordinated activities of three enzymes, AMV reverse transcriptase, RNaseH, and T7RNA polymerase. Quantitative detection is achieved by way of internal calibrators, which are added at isolation, which are coamplified and subsequently identified along with the wild-type of RNA using a suitable means such as electrochemiluminescence.

Table 1 below shows labeling strategies for incorporating a photosensitizer-labeled nucleotide within the target nucleic acid or probe. Furthermore, Table 1 shows that an aminofunctionalized nucleic acid (for example, an oligonucleotide probe or PCR primer) may be labeled by reaction with an NHS ester form of a sensitizer.

TABLE I

Labeling Strategies For Nucleic Acids

| Procedure | Labeled Compound |
|---|---|
| Incorporation of Labels by PCR | dUTP, primers |
| Random Primed DNA Labeling | dUTP, hexamers |
| Labeling of RNA with RNA polymerase (NASBA) | UTP, primers |
| Labeling by Nick Translation | dUTP |
| 3′-Labeling of ssDNA with Terminal Transferase | (d)dUTP |
| Labeling of Aminofunctionalized Nucleic Acids | NHS Ester |

Figure 8:
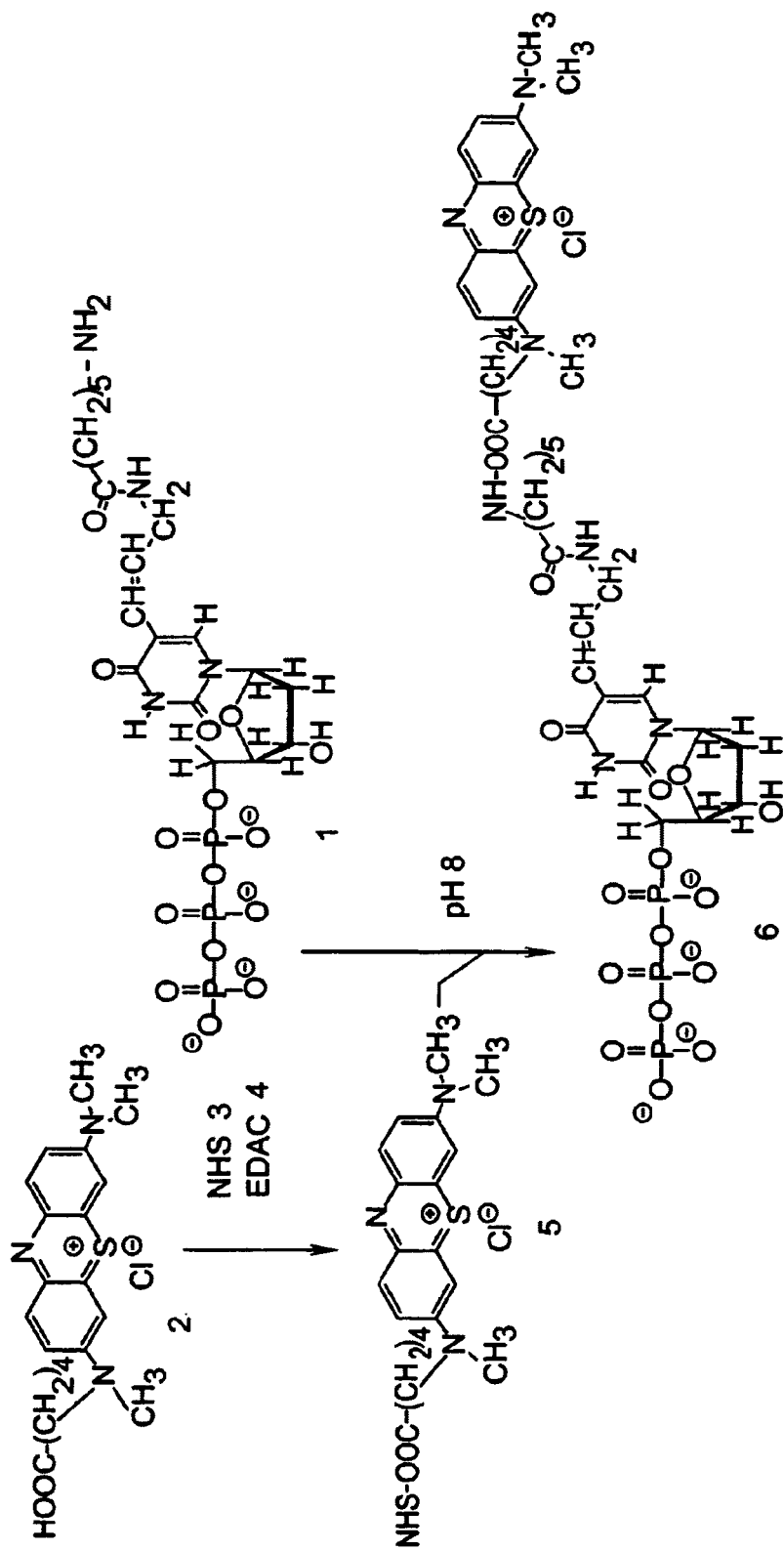
FIG. 8 shows the synthesis of sensitizer-labeled dUTP.
Figure 9:
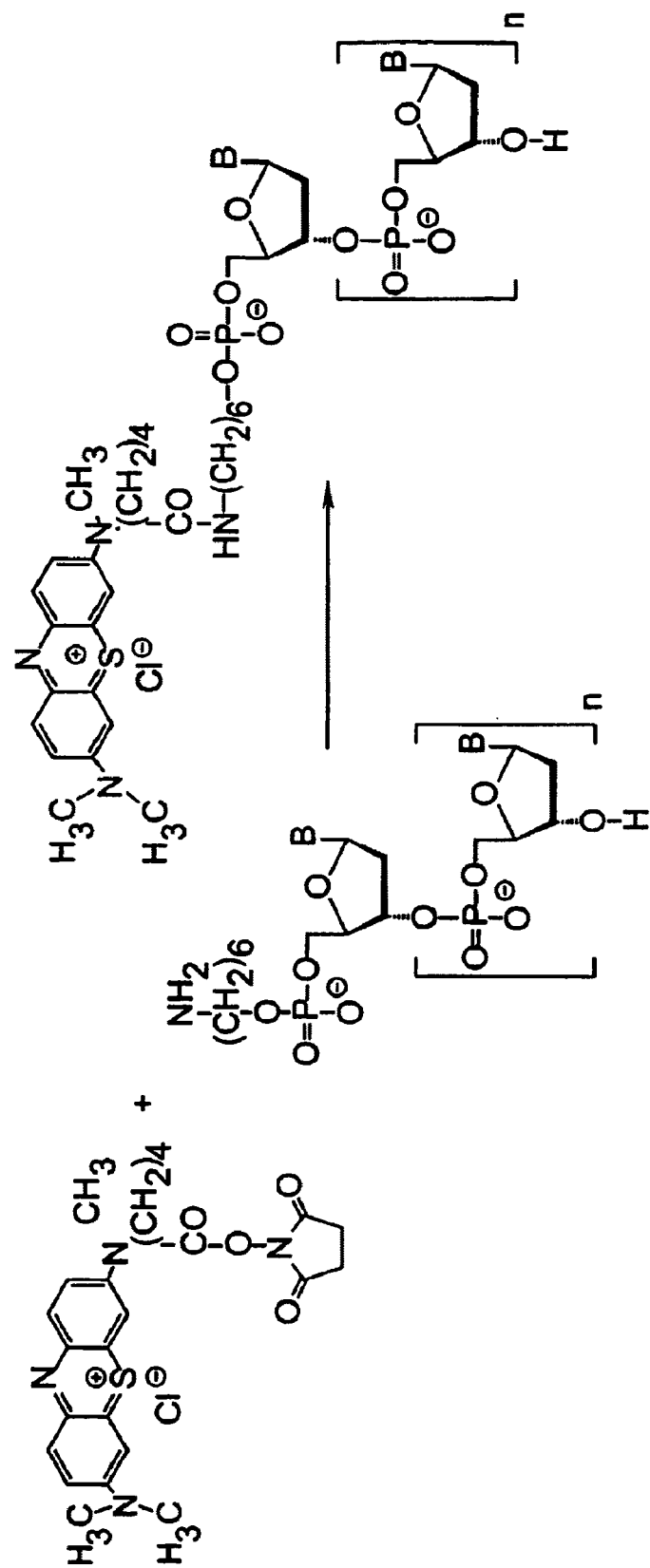
FIG. 9 shows the 5'-labeling of an aminofunctionalized nucleic acid.

We refer now to FIG. 8, which shows the synthesis of a sensitizer-labeled dUTP. In particular, the methylene blue sensitizer (compound 2) is reacted with N-hydroxysuccinimide (compound 3) and EDAC (1-ethyl- 3-(3 dimethylaminopropylcarbodiimide) (compound 4) to form the activated ester form of the sensitizer (compound 5). The activated ester form is reacted with aminofunctionalized dUTP (compound 1) at pH 8 to form the sensitizer-labeled dUTP (compound 6), which may be incorporated as a building block within an analyte to be detected. Moreover, as shown in FIG. 9, an N-hydroxysuccinimide ester form of methylene blue may be reacted with an aminofunctionalized nucleic acid. For example, an aminofunctionalized oligonucleotide primer may react with the activated ester in order to obtain a 5'-labeled primer useful for PCR incorporation of the label within the analyte.

According to the present invention, a useful sensitizer or photosensitizer is any label directly or indirectly bound to the analyte that, when excited by radiation of a particular wavelength or other physical or chemical stimulus, can achieve an excited state (e.g. a triplet state). In one desired embodiment, a useful sensitizer is one which can interact with triplet oxygen to form singlet oxygen. The sensitizer may be selected from, but is not limited to, methylene blue, rhodamine, perylene, aromatic hydrocarbons, heterocyclic compounds, eosin, free porphyrins, metalloporphyrins, tetraphenylporphine, phthalocyanine, chlorins, flavin derivatives, xanthines, phenothiazines, acridines, acridans, and combinations thereof.

As described above, sensitizers may be linked to the analyte by methods which are well known in the art, including by use of one or more functional groups chemically bound to the sensitizer that react with a complimentary functional group associated with the analyte or agent probative of the analyte or, alternatively, with a complimentary functional group associated with a building block of the analyte or probe. For example, with further reference to FIGS. 8 and 9, a sensitizer dye may be bound to an analyte or probative agent using a functional group such as an N-hydroxysuccinimidyl ester linker to react with a complimentary amine linking group to allow for incorporation of the sensitizer via an amide group into a nucleotide of a nucleic acid. In one embodiment, the sensitizer is first incorporated into the building block and the building block is thereafter incorporated within the analyte.

The following examples are provided, but are not intended to limit the scope or spirit of the invention in any way.

EXAMPLE 1
Sensitizer-Labeling of Oligonucleotide
Modified methylene blue derivatives were obtained according to procedures described by Motsenbocker, et al. in Photochemistry & Photobiology vol. 58, pp. 648–652, 1993. The terminal carboxy group of an activated N-hydroxysuccinimidyl ester form of the methylene blue sensitizer was coupled to a 5'-aminomodified oligonucleotide using standard methods known in the art. (Ruth, J. L., in Oligonucleotides and Analogues: A Practical Approach, Eckstein (Editor), pp. 255–280, Oxford University Press, NY 1991). The oligonucleotide was complementary in sequence to cDNA encoding alcohol dehydrogenase. The 5'-aminomodified oligonucleotides used for labeling with methylene blue as well as unmodified oligonucleotides used for PCR amplification of the target alcohol dehydrogenase cDNA were synthesized on a PE Biosystems Nucleic Acid Synthesizer, Model No. ABI 3948.

EXAMPLE 2
Dot Blot Hybridization of Methylene Blue-Labeled Oligonucleotide to Target DNA Following PCR amplification of the target DNA, said DNA was spotted on a Hybond+nylon membrane (Amersham Biosciences Corporation), along with negative controls of linearized pUC19 DNA at various concentrations ranging from 25 to 500fmoles in a total volume of 1 microliter. Spots were allowed to dry. The DNA was subsequently denatured and fixed as follows: 1 minute soak in 1.5 M NaCl; 0.5 M NaOH, followed by fixation by baking at 120° C. for 40 minutes, followed by 5 minute soak in 1.5 M NaCl; 0.5 M Tris-Cl pH 7.5. Hybridization was as follows: The filter membrane was soaked in prehybridization buffer (0.25 M Na-PO$_4$; pH 7.2; 7% (w/v) SDS for 45 minutes at 40° C. in a total volume of 0.5 ml per cm$^2$/membrane. The labeled oligonucleotide probe was added directly to the prehybridization buffer at a final concentration of about 2 $\mu$moles/ml and incubated for 16 h at 40° C. The hybridized membrane was washed in a buffer of 6×SSC at room temperature for two times at 5 minutes each wash followed by two times at 5 minutes each wash in 3×SSC at 40° C. to remove nonstringent or background hybridization. SSC (1×) is 0.15 M NaCl, 0.015 M sodium citrate (pH 7.0).

EXAMPLE 3
Preparation of the Inventive Film
Ten mg of an appropriate chemiluminescent olefin are dissolved in 100 ml (0.37 mM) of n-hexane or methanol. A Hybond-N neutral nylon membrane (Amersham Biosciences Corporation) was dipped in the olefin solution and allowed to air dry.

EXAMPLE 4
Formation of a Triggerable Chemiluminescent Compound on the Inventive Film Hybridization was detected by first assembling the sandwich formation shown in FIG. 6A. In order to detect a signal, a membrane containing hybridized target DNA from Example 2 is placed (DNA side up) on a glass plate. The inventive membrane with chemiluminescent precursor immobilized therewith was subsequently placed on top of the membrane with the target molecule. A sheet of nontransparent, black paper is placed over the inventive film and another glass plate was placed on top of the whole sandwich formation. The sandwich formation was then exposed to red light for 15 minutes by using an appropriate cut-off filter and inrradiating through the glass plate containing the hybridized target DNA. This allows for formation of a triggerable chemiluminescent precursor compound on the inventive film, which may be subsequently triggered as described in Example 5 below.

EXAMPLE 5
First Method for Triggering of the Chemiluminescent Compound on the Inventive Film A sandwich formation similar to that shown in FIG. 6B was formed in the present example. In the dark, a sheet of Hyperfiln ECL (Amersham Biosciences Corporation) was placed in a cassette and a sheet of transprent plastic film was placed on top of this to protect the x-ray film from the basic solution used for chemical triggering of the triggerable chemiluminescent compound (i.e., dioxetane). The inventive membrane, containing the triggerable chemiluminescent compound formed in Example 4 was then placed on top of the plastic film, with the DNA side toward the x-ray film. A solution of 0.1 M NaOH was used for activation of the triggerable chemiluminescent compound present on the

13 inventive film. The film was developed using standard techniques and successful hybridization between the labeled probe and the target DNA was observed as black spots on the Hyperfilm ECL with the lowest quantity of DNA detected being in the range of 25 fmoles.

EXAMPLE 6
Second Method for Triggering of the Chemiluminescent Compound Formed on the Inventive Film Similar to Example 4 above, hybridization between the target DNA and methylene blue-labeled oligonucleotide was detected by first briefly (less than 5 seconds) dipping a nylon membrane (Hiybond+nylon membrane from Amersham Biosciences Corporation) in an olefin solution (10 mg olefin dissolved in 100 ml (0.37 mM) of n-hexane or methanol followed by air drying In order to detect a signal, a sheet of filter paper previously soaked in a saturated solution of ammonium carbonate and then dried to a solid form was taped to a glass plate. The inventive membrane with the triggerable chemiluminescent compound thereon formed in Example 4 was placed on top of the filter paper containing the dried base (DNA side up) and a piece of plastic was placed on top of this. In the dark, a sheet of Hyperfilm ECL (Amersham Biosciences Corporation) was placed over the plastic sheet and a glass plate was placed on top. The whole sandwich formation was incubated at 80° C. for 15 minutes to allow for release of the base from the filter paper and result in activation of the chemiluminescent compound present on the inventive filn. The film was developed using standard techniques as successfil hybridization was observed as black spots on the Hyperfilm ECL with the lowest quantity of DNA detected being in the range of 25 fmoles.

EXAMPLE 7
Sensitizer-Labeling of an Antibodv or Antigen

A modified methylene blue derivative is obtained according to procedures described by Motsenbocker, et al. in Photochemistry & Photobiology, vol. 58, pp. 648–652, 1993. The terminal carboxy group of an activated N-hydroxysuccinimidyl ester form of the methylene blue sensitizer is coupled to an antibody or antigen via the terminal amino group using standard methods known in the art. The antibody probe used is specific for an antigen target molecule or alternatively, an antigen probe is specific for an antibody target molecule.

EXAMPLE 8
Immunoassay for Detection of Binding of Sensitizer-labeled Antibody Probe to Target Antigen Molecules Antigen was spotted on a nitrocellulose, PVDF or nylon membrane in various concentrations. The membrane was subsequently blocked in a solution of 0.2% casein/0.1% Tween 20 detergent in aqueous phosphate buffered saline solution (PBS) for 1 hour, following which a 1/2000 to 1/5000 dilution (in 0.2% casein/PBS) of methylene blue-labeled antibody (at 1 µg monoclonal Ab in 40 µl PBS) was added, wherein the antibody was specific for the target antigen molecule. The membrane was then incubated for 1 hour at room temperature and washed five times (for 5 minutes each time) in 0.3% Tween 20 detergent in PBS, and one time in PBS at room temperature for 5 minutes to remove non-specific or non-stringent binding.

EXAMPLE 9
Method of Detecting Target Antigen Hybridized to Methylene Blue-labeled Antibody Sandwich format assays used for detection of the hybridized target antigen are the same as those described in Examples 4 through 6 above.

What is claimed is:

1. A method of detecting polynucleotide analytes using chemiluminescence comprising the steps of:
   (a) providing a first film including a complex comprising a polynucleotide analyte bound to a sensitizer or a sensitizer-labeled probe;
   (b) providing a second film comprising at least one solid chemiluminescent precursor component immobilized therewith that is capable of producing a triggerable chemiluminescent compound;
   (c) placing said first and second films in sufficient proximity to each other to permit singlet oxygen produced from excitation of the sensitizer on said first film and to react with said chemiluminescent precursor on said second film;
   (d) exposing said films to suitable conditions to form said triggerable chemiluminescent compound on said second film;
   (e) allowing said triggerable chemiluminescent compound to be triggered by an activating source to produce a detectable light signal on said second film; and
   (f) detecting and/or recording said resultant signal on said second film.

2. The method of claim 1, wherein said polynucleotide analyte is selected from the group consisting of oligonucleotides, polynucleotides, single-stranded DNA, double-stranded DNA, DNA-RNA duplexes, mRNA, rRNA, tRNA and analogs thereof.

3. The method of claim 1, wherein the sensitizer-labeled probe is complementary in sequence to the polynucleotide analyte.

4. The method of claim 1, wherein the sensitizer is selected from the group consisting of methylene blue, rhodamine, perylene, aromatic hydrocarbons, heterocyclic compounds, cosin, free porphyrins, metalloporphyrins, tetraphenylporphine, phthalocyanine, chlorins, flavin derivatives, xanthines, phenothiazines, acridines, acridans, and combinations thereof.

5. The method of claim 1, wherein said suitable conditions comprises the combination of light and oxygen.

6. The method of claim 1, wherein said chemiluminescent precursor component is an olefin selected from the group consisting of enol ethers, enamines, 9-alkylidene-N-alkylacridans, arylvinylethers, arylimidazoles, 9-alkylidene-xanthenes and lucigenin.

7. The method of claim 6, wherein the chemiluminescent olefin is covalently bound to a fluorescent molecule which firther enhances chemical detection.

8. The method of claim 1, wherein said triggerable chemiluminescent compound is a 1,2-dioxetane.

9. The method of claim 1, wherein step (a) comprises incorporating a sensitizer-labeled nucleotide or sensitizer-labeled primer into said polynucleotide analyte or probe.

10. The method of claim 9, wherein said sensitizer-labeled primer is a random or specific primer.

11. The method of claim 9, wherein said sensitizer-labeled nucleotide or primer is incorporated into said polynucleotide analyte or probe during a nucleic acid amplification reaction.

12. The method of claim 11, wherein said nucleic acid amplification reaction is a Polymerase Chain Reaction (PCR) or Nucleic Acid Sequence Based Amplification (NASBA).

13. The method of claim 9, wherein said sensitizer-labeled nucleotide or primer is incorporated into said polynucleotide analyte or probe during a reaction selected from the group consisting of a primer extension reaction, an in vitro transcription reaction, a nick translation reaction, and a terminal transferase reaction.

14. The method of claim 1, wherein the sensitizer includes a chemical linker.

15. The method of claim 14, wherein step (a) further comprises reacting said chemical linker with a complementary linking group in the polynucleotide analyte or probe.

16. The method of claim 1, wherein step (a) comprises immobilizing said polynucleotide analyte to said first film.

17. The method of claim 16, wherein step (a) further comprises hybridizing said sensitizer-labeled probe to said immobilized polynucleotide analyte.

18. The method of claim 1, wherein said exposing step further comprises electronically exciting the sensitizer to a triplet state by exposure to one or more of the stimulus selected from the group consisting of radiation, electron transfer, electrolysis, and electroluminescence.

19. The method of claim 18, wherein said radiation comprises light having awavelength from about 30 nm to about 1,100 nm.

20. The method of claim 18, wherein said exposing step further comprises generating singlet oxygen from the reaction of molecular oxygen with the excited sensitizer.

21. The method of claim 1, wherein said first film is a polymeric film.

22. The method of claim 1, wherein said first film is a glass, metal, textile, paper or cellulose film.

23. The method of claim 1, wherein said activating source is selected from the group consisting of heat, chemical treatment, electrical treatment, enzymatic treatment and combinations thereof.

24. The method of claim 1, further comprising the step of providing a third film for contact with said second film, said third film comprising at least one solid chemical component immobilized on or impregnated therewith which when acted upon by an energy source releases an activating substance, which activating substance in the presence of the triggerable cheiniluminescent compound present on said second film, reacts therewith to produce said detectable light signal on the second film.

25. The method of claim 24, wherein the solid chemical component is selected from the group consisting of acids, bases, salts, enzymes, inorganic and organic catalyst, electron donor sources and combinations thereof.

26. The method of claim 24, wherein the energy source is selected from the group consisting of hydration energy, thermal energy, electromagnetic energy, electrical energy, mechanical energy and combinations thereof.

27. The method of claim 25, wherein the enzyme is selected from the group consisting of alkaline phosphatase and horseradish peroxidase.

28. The method of claim 24, wherein the triggerable chemiluminescent compound contains a labile group removable by enzymatic cleavage.

29. A method of preparing a chemiluminescent assay comprising the steps of:
(a) providing a first film including a complex comprising a polynucleotide analyte bound to a sensitizer or a sensitizer-labeled probe;
(b) providing a second film comprising at least one solid chemiluminescent precursor component immobilized therewith that is capable of producing a triggerable chemiluminescent compound;
(c) positioning said first and second films in overlapping contact with each other;
(d) exposing said contacted films to suitable conditions to form the triggerable chemiluminescent compound on the second film; and
(e) allowing said triggerable chemiluminescent compound to be triggered by an activating source to produce a detectable light signal on said second film.

30. The method of claim 29, wherein said polynucleotide analyte is selected from the group consisting of oligonucleotides, polynucleotides, single-stranded DNA, double-stranded DNA, DNA-RNA duplexes, mRNA, rRNA, tRNA and analogs thereof.

31. The method of claim 29, wherein the sensitizer-labeled probe is complementary in sequence to the polynucleotide analyte.

32. The method of claim 29, wherein the sensitizer is selected from the group consisting of methylene blue, rhodamine, perylene, aromatic hydrocarbons, heterocyclic compounds, eosin, free porphyrins, metalloporphyrins, tetraphenylporphine, phthalocyanine, chlorins, flavin derivatives, xanthines, phenothiazines, acridines, acridans, and combinations thereof.

33. The method of claim 29, wherein step (a) comprises incorporating a sensitizer-labeled nucleotide or sensitizer-labeled primer into said polynucleotide analyte or probe.

34. The method of claim 33, wherein said sensitizer-labeled nucleotide or primer is incorporated into said polynucleotide analyte or probe during a nucleic acid amplification reaction.

35. The method of claim 34, wherein said nucleic acid amplification reaction is a Polymerase Chain Reaction (PCR) or Nucleic Acid Sequence Based Amplification (NASBA).

36. The method of claim 33, wherein said sensitizer-labeled nucleotide or primer is incorporated into said polynucleotide analyte or probe during a reaction selected from the group consisting of a primer extension reaction, an in vitro transcription reaction, a nick translation reaction, and a terminal transferase reaction.

37. The method of claim 29, wherein the sensitizer includes a chemical linker.

38. The method of claim 37, wherein step (a) further comprises reacting said chemical linker with a complementary linking group in the polynucleotide analyte or probe.

39. The method of claim 29, wherein step (a) comprises immobilizing said polynucleotide analyte to said first film.

40. The method of claim 39, wherein step (a) firther comprises hybridizing said sensitizer-labeled probe to said immobilized polynucleotide analyte.

41. The method of claim 29, wherein said exposing step firther comprises electronically exciting the sensitizer to a triplet state by exposure to one or more of the stimulus selected from the group consisting of radiation, electron transfer, electrolysis, and electroluminescence.

42. The method of claim 29, wherein said suitable conditions comprises the combination of light and oxygen.

43. The method of claim 29, wherein said chemiluminescent precursor is an olefin selected from the group consisting of enol ethers, enamines, 9-alkylidene-N-alkylacridans, arylvinylethers, arylimidazoles, 9-alkylidene-xanthenes and lucigenin.

44. The method of claim 29, wherein the triggerable chemiluminescent compound is a 1,2-dioxetane.

45. The method of claim 29, wherein the activating source is selected from the group consisting of heat, chemical treatment, electrical treatment, enzymatic treatment and combinations thereof.

46. The method of claim 29, further comprising the step of providing a third film for contact with said second film, said thid film comprising at least one solid chemical component immobilized on or impregnated therewith which when acted upon by an energy source releases an activating substance, which activating substance in the presence of the triggerable chemiluminescent compound present on said second film, reacts therewith to produce said detectable light signal.

47. The method of claim 46, wherein the solid chemical component is selected from the group consisting of acids, bases, salts, enzymes, inorganic and organic catalyst, electron donor sources and combinations thereof.

48. The method of claim 46, wherein the energy source is selected from the group consisting of hydration energy, thermal energy, electromagnetic energy, electrical energy mechanical energy and combinations thereof.

49. A chemiluminescent assay kit comprising:
(a) a first film component comprising a solid film substrate and at least one chemiluminescent precursor immobilized therewith that is capable of producing a triggerable chemiluminescent compound, said film component being free of compounds which generate singlet oxygen and being adapted for use with a sensitizer-labeled polynucleotide analyte or agent probative of the analyte; and (b) a sensitizer-labeled nucleotide and/or a sensitizer-labeled primer.

50. The kit of claim 49, wherein said probative agent is complementary in sequence to the polynucleotide analyte.

51. The kit of claim 49, wherein said primer is a random or specific primer.

52. The kit of claim 49, wherein said nucleotide is a ribonucleotide, a deoxyribonucleotide or a dideoxyribonucleotide.

53. The kit of claim 49, further comprising an activator for triggering a chemiluminescent compound.

54. The kit of claim 53, wherein said activator is immobilized on a second film.

55. The kit of claim 49, wherein said sensitizer-labeled nucleotide is capable of being introduced into said analyte or said probative agent.

56. The kit of claim 49, wherein said sensitizer-labeled primer is capable of being introduced into said analyte or said probative agent.

* * * * *

UNITED STATES PATENT AND TRADEMARK OFFICE
CERTIFICATE OF CORRECTION

PATENT NO. : 6,911,305 B2
DATED : June 28, 2005
INVENTOR(S) : Levison et al.

It is certified that error appears in the above-identified patent and that said Letters Patent is hereby corrected as shown below:

Column 1,
Line 29, should read -- ...nonchemical assays wherein... --.

Column 4,
Line 11, should read -- ...a first film having bound... --.

Column 12,
Line 59, should read -- ...a sheet of transparent plastic film... --.

Column 13,
Line 28, should read -- ...the inventive film... --.

Column 14,
Line 49, should read -- ...which further enhances... --.

Column 15,
Line 18, should read -- ...having a wavelength from... --.
Line 37, should read -- ...chemiluminescent compound... --.

Column 16,
Line 47, should read -- ...step further comprises... --.
Line 66, should read -- ...said third film... --.

Signed and Sealed this

Sixth Day of September, 2005

JON W. DUDAS
*Director of the United States Patent and Trademark Office*